US010750691B2

(12) United States Patent
Wargent (10) Patent No.: US 10,750,691 B2
(45) Date of Patent: Aug. 25, 2020

(54) METHODS OF SEED TREATMENT AND RESULTING PRODUCTS (71) Applicant: BIOLUMIC LIMITED, Palmerston North (NZ)

(72) Inventor: Jason John Wargent, Palmerston North (NZ)

(73) Assignee: BIOLUMIC LIMITED, Palmerston North (NZ)

( * ) Notice: Subject to any disclaimer, the term of this patent is extended or adjusted under 35 U.S.C. 154(b) by 0 days.

(21) Appl. No.: 14/857,486

(22) Filed: Sep. 17, 2015

(65) Prior Publication Data
US 2016/0073599 A1   Mar. 17, 2016

(30) Foreign Application Priority Data

Sep. 17, 2014 (NZ) ........................................ 700157

(51) Int. Cl.
*A01H 3/02* (2006.01)
*A01C 1/00* (2006.01)
*A01G 7/00* (2006.01)
*A01G 22/00* (2018.01)

(52) U.S. Cl.
CPC ................. *A01H 3/02* (2013.01); *A01C 1/00* (2013.01); *A01G 7/00* (2013.01); *A01G 22/00* (2018.02)

(58) Field of Classification Search
None
See application file for complete search history.

(56) References Cited

U.S. PATENT DOCUMENTS

| | | | |
|---|---|---|---|
| 7,348,475 B2 | 3/2008 | Shin et al. | |
| 8,001,722 B2 | 8/2011 | Wilson et al. | |
| 8,845,149 B2 | 9/2014 | Cheng et al. | |
| 2008/0120736 A1 | 5/2008 | Hurst | |
| 2008/0298052 A1 | 12/2008 | Hurst et al. | |
| 2009/0272029 A1 | 11/2009 | Aiking et al. | |
| 2010/0193707 A1 | 8/2010 | Yamada et al. | |
| 2012/0054061 A1 | 3/2012 | Fok et al. | |
| 2013/0008085 A1 | 1/2013 | Aikala et al. | |
| 2013/0294065 A1 | 11/2013 | Wells | |
| 2014/0204567 A1 | 7/2014 | Cheng et al. | |
| 2016/0345512 A1 | 12/2016 | Wargent | |
| 2017/0000041 A1 | 1/2017 | Wargent | |

FOREIGN PATENT DOCUMENTS

| | | |
|---|---|---|
| CN | 103999748 A | 8/2014 |
| DE | 19900616 A1 | 7/2000 |
| EP | 1300066 A1 | 4/2003 |
| EP | 2172097 A1 | 4/2010 |
| JP | 2001028947 A | 2/2001 |
| JP | 2004166638 A | 6/2004 |
| JP | 2005328734 A | 12/2005 |
| JP | 2006158262 A | 6/2006 |
| JP | 2010094109 A | 4/2010 |
| JP | 2013051939 A | 3/2013 |
| JP | 2013153691 A | 8/2013 |
| NZ | 702063 A | 11/2016 |
| TW | M458082 U | 8/2013 |
| WO | WO-0051414 A1 | 9/2000 |
| WO | WO-2012040838 A1 | 4/2012 |
| WO | WO-2012085336 A1 | 6/2012 |
| WO | WO-2015119510 A1 | 8/2015 |
| WO | WO-2015137825 A1 | 9/2015 |
| WO | WO-2016043605 A1 | 3/2016 |
| WO | WO-2016054268 A1 | 4/2016 |
| WO | WO-2019002946 A1 | 1/2019 |
| WO | WO-2019038594 A2 | 2/2019 |

OTHER PUBLICATIONS

Shaukat et al. Effect of supplemental UV-B irradiation on germination, seedling growth, and biochemical responses of sunflower (*Helianthus annuus* L.). (2011), Fuuast J. Biol., 1(1):27-33.*
Siddiqui et al. Effect of UV-B radiation on seed germination, plant height, foliage and seed yield of soybean (*Glicine max* L. Merrill). Prog. Agric. 7 (1/2): 42-45 (2005).*
Li et al. Effect of UV-B radiation on seed germination and seedling growth of *Arabidopsis*. Chin. Bull. Bot. (2013), vol. 48, pp. 52-58.*
Jenkins. Signal transduction in responses to UV-B radiation. Ann. Rev. Plant Biol. 2009;60:407-31.*
Mishra, A. Effect of UVB radiation on seed germination, seedling growth, photosynthetic pigments and biochemical responses of postum sativum (L.). Photosynthetic Pigments and Biochemical Responses of Pistum Sativum (L.) Zenith International Journal of Multidisciplinary Research, vol. 5(1), pp. 124-129 (2015).
Behn, H. et al. Development-dependent UV-B Responses in Red Oak Leaf Lettuce (*Lactuca sativa* L.): Physiological Mechanisms and Significance for Hardening, European Journal of Horticultural Science vol. 76, No. 2, pp. 33-40 (Jul. 2011).
Davey, M.P. et al. The UV-B photoreceptor UVR8 promotes photosynthetic efficiency in *Arabidopsis thaliana* exposed to elevated levels of UV-B, Photosynthesis Research, 2012, vol. 114, pp. 121-131.
Favory et al. Interaction of COP1 and UVR8 regulates UV-B-induced photomorphogenesis and stress acclimation in *Arabidopsis*, Embo Journal, 28(5); 591-601 (2009).
Heil et al. Induced systemic resistance (ISR) against pathogens—a promising field for ecological research, Perspectives in Plant Ecology, Evolution and Systematics, vol. 4, 2001, pp. 65-79.
IARC Monographs on the Evaluation of Carcinogenic Risks to Humans. vol. 55—Solar and ultraviolet radiation; Chapter 1; Exposure data (1992) (International Agency for Research on Cancer—World Health Organization).
Ibdah et al. Spectral dependence of flavonol and betacyanin accumulation in Mesembryanthemum crystallinum under enhanced ultraviolet radiation, Plant, Cell and Environment 25: 1145-1154 (2002).
International Application No. PCT/NZ2015/000008 International Preliminary Report on Patentability dated Apr. 19, 2016.

(Continued)

*Primary Examiner* — Cynthia E Collins
(74) *Attorney, Agent, or Firm* — Wilson Sonsini Goodrich & Rosati (57) ABSTRACT

A method of treating a seed for sowing is provided for improving subsequent plant performance comprising the step of treating the seed for sowing with UV-B irradiation.

21 Claims, 3 Drawing Sheets

(56) References Cited

OTHER PUBLICATIONS

International Application No. PCT/NZ2015/000008 Written Opinion dated Jan. 14, 2016.
International Application No. PCT/NZ2015/000014 International Preliminary Report on Patentability dated Nov. 16, 2015.
International Application No. PCT/NZ2015/000014 Written Opinion dated Jun. 3, 2015.
International Application No. PCT/NZ2015/050153 International Search Report dated Nov. 23, 2015.
International Application No. PCT/NZ2015/050153 Written Opinion dated Feb. 18, 2016.
Jenkins, G.I. Signal Transduction in Responses to UV-B Radiation, Annual Review of Plant Biology, vol. 60, 2009, pp. 407-431.
Kubasek, W.L. et al. Regulation of flavonoid biosynthetic genes in germinating *Arabidopsis* seedlings, The Plant Cell, 1992, vol. 4, pp. 1229-1236.
Marzocca, A. et al. Tratamiento de semillas de 'Kok-saghyz' con rayos ultravioletas, Revista de Investigaciones Agricolas, 1957, vol. XI, pp. 227-245.
Sosa-Flores, V. P. et al. Study of morphological and histological changes in melon plants grown from seeds irradiated with UV-B, Journal of Applied Horticulture, Oct.-Dec. 2014, vol. 16, pp. 199-204.
Rizzini, L. et al. Perception of UV-B by the *Arabidopsis* UVR8 Protein, Science vol. 332, No. 6025; pp. 103-106 (2011).
Rozema, J. et al. UV-B as an environmental factor in plant life: stress and regulation, Trends in Ecology & Evolution, vol. 12, 1997, pp. 22-28.
Shaukat, S.S., et al. Effect of Supplemental UV-B Radiation on Germination, Seedling Growth, and Biochemical Responses of Sunflower (*Helianthus annuus* L.). Fuuast Journal of Biology vol. 1, No. 1, pp. 27-33 (2011).
Siddiqui, S. et al. Effect of UV-B radiation on seed germination, plant height, foliage and seed yield of soybean (*Glicine max* L. *Merrill*), Progressive Agriculture, 2007, vol. 7, pp. 42-45.
Vallad et al. Systemic Acquired Resistance and Induced Systemic Resistance in Conventional Agriculture, Crop Science, vol. 44: 1920-1934 (2004).
Vyn, T.J. et al. Potassium fertilization effects on isoflavone concentrations in soybean [*Glycine max* (L.) *Merr*.], Journal of Agricultural and Food Chemistry, 2002, vol. 50, pp. 3501-3506.
Wargent, J.J. et al. Increased exposure to UV-B radiation during early development leads to enhanced photoprotection and improved long-term performance in Lactuca sativa, Plant, Cell & Environment, 2011, vol. 34, pp. 1401-1413.
Wu, M. et al. Computational Evidence for the Role of *Arabidopsis thaliana* UVR8 as UV-B Photoreceptor and Identification of Its Chromophore Amino Acids, Journal of Chemical Information and Modeling, 2011, vol. 51, pp. 1287-1295.
International Application No. PCT/IB2017/001152 International Search Report and Written Opinion dated Nov. 8, 2017.
European Application No. 15841342.7 European Search Report dated Feb. 13, 2018.
Kakani, VG et al. Field crop responses to ultraviolet-B radiation: a review. Agricultural and Forest Meteorology, 120(1-4):191-218 (Dec. 24, 2003).
Liu, Bing et al. Effects of enhanced UV-B radiation on seed growth characteristics and yield components in soybean. Field Crops Research, 15:158-163 4(2013).
Ozbolt, L. et al. Distribution of selenium and phenolics in buckwheat plants grown from seeds soaked in Se solution and under different levels of UV-B radiation. Food Chemistry 110(3):691-696 (Oct. 1, 2008).
European Application No. 15761440.5 Extended European Search Report dated Sep. 19, 2017.
European Patent Application No. EP15746659.0 Extended European Search Report dated Oct. 11, 2017.
Besteriro, et al. *Arabidopsis* MAP kinase phosphatase 1 and its target MAP kinases 3 and 6 antagonistically determine UV-B stress tolerance, independent of the UVR8 photoreceptor pathway, Plant Journal, 58: 727-737 (2011).
Jansen, M., Low threshold levels of ultraviolet-B in a background of photosynthetically active radiation trigger rapid degradation of the D2 protein of photosystem—II, The Plant Journal, 9(5): 693-699 (1996).
Li, X. et al. Effect of UV-B irradiation on seed germination and seedling growth of *Arabidopsis*, Chinese Bulletin of Botany, 2013, vol. 48, pp. 52-58.
Musil, C.F. et al. Ultraviolet-B Irradiation of Seeds Affects Photochemical and Reproductive Performance of the Arid-Environment Ephemeral Dimorphotheca Pluvialis, Environmental and Experimental Botany, 34(4): 371-378 (1994).
Qaderi, M., et al. Morphological and physiological responses of canola (*Brassica napus*) siliquas and seeds to UVB and $CO_2$ under controlledenvironment conditions, Environmental and Experimental Botany 60: 428-437 (2007).
Setlow, R.B. The Wavelengths in Sunlight Effective in Producing Skin Cancer: A Theoretical Analysis, Proc. Acad. Nat. Sci., 71: 3363-3366. (1974).
Tepfer, et al. Survival of Plant Seeds, Their UV Screens, and nptII DNA for 18 Months Outside the International Space Station Astrobiology, 12: 517-528 (2012).
Chen et al. Shoot-to-Root Mobile Transcription Factor HY5 Coordinates Plant Carbon and Nitrogen Acquisition. Curr Biol 26(5):640-646 (Mar. 2016).
Cluis e tal. The *Arabidopsis* transcription factor HY5 integrates light and hormone signaling pathways. Plant J 38(2):332-347 (2004).
Ebisawa et al. Supplementary ultraviolet radiation B together with blue light at night increased quercetin content and flavonol synthase gene expression in leaf lettuce (*Lactuca sativa* L.). Environmental Control in Biology 46(1):1-11 (2008).
European Patent Application No. 15761440.5 Summons to Attend Oral Proceedings Pursuant to Rule 115(1) EPC dated Jun. 4, 2019.
Folta et al. Light as a Growth Regulator: Controlling Plant Biology with Narrow-bandwidth Solid-state Lighting Systems. Hortscience 43:1957-1964 (2008).
Gangappa et al. The Multifaceted Roles of HY5 in Plant Growth and Development. Mol Plant 9(10):1353-1365 (Oct. 2016).
Huche-Thelier et al. Light signaling and plant responses to blue and UV radiations—Perspectives for applications in horticulture. Environmental and Experimental Botany, Elsevier, Amsterdam, NL 121:22-38 (2015).
International Application No. PCT/IB2018/000839 International Search Report and Written Opinion dated Oct. 18, 2018.
International Application No. PCT/IB2018/001056 International Search Report and Written Opinion dated Apr. 3, 2019.
Lee et al. Analysis of transcription factor HY5 genomic binding sites revealed its hierarchical role in light regulation of development. Plant Cell 19(3):731-749 (2007).
Lydon et al. UV-B Radiation Effects on Photosynthesis. Growth and Cannabinoid Production of Two Cannabis Sativa Chemotypes. Photochemistry and Photobiology 46(2):201-206 (1987).
Peykarestan et al., Uv irradiation effects on seed germination and growth, protein content, peroxidase and protease activity in redbean. International Research Journal of Applied and Basic Sciences. 3(1):92-102 (2012).
Tegelberg et al., Red : far-red light ratio and UV-B radiation: their effects on leaf phenolics and growth of silver birch seedlings. Plant, Cell & Environment. 27(8):1005-1013 (2004).
U.S. Appl. No. 14/857,486 Office Action dated May 16, 2019.
U.S. Appl. No. 15/117,157 Office Action dated Apr. 3, 2019.
U.S. Appl. No. 15/125,698 Office Action dated Apr. 25, 2019.
Zoratti et al. Light-controlled flavonoid biosynthesis in fruits. Frontiers in Plant Science 5(534):16 pgs (2014).

* cited by examiner

METHODS OF SEED TREATMENT AND RESULTING PRODUCTS

CROSS-REFERENCE

This application claims the benefit of New Zealand Application No. 700157, filed on Sep. 17, 2014, which is incorporated herein by reference in its entirety.

BACKGROUND

This invention relates to methods of seed treatment and resulting products.

There is an important societal and commercial impetus to find ways of improving yield and quality of crops primarily for human consumption, and doing so in a safe and sustainable manner. Of course, there has been a long felt need and motivation to do so over most of our agricultural history. Yet over the past two centuries it has become even more pressing due to the rapid expansion of the human population, and there is a need to be as efficient as possible with the arable land available for crop production. To put this into context, the United Nations estimated the world's human population stood at one billion in about 1800, three billion in 1960, seven billion in 2011, and expects it to rise to over nine billion by 2050.

With a substantial increase in scientific understanding of plant genetics and biology over the past few decades, substantial research has focused on methods to improve quality and yield of crops, both from academic and commercial viewpoints. The main focus has been to develop new ways to improve resistance to abiotic and biotic stresses including drought, high visible light stress, insect pest damage, and fungal pathogen infection, to name a few. The commonly accepted theory is, if the seed and/or resulting plant has suitable defences in place, overall plant performance will be improved, and the downstream result should be an increased yield and/or quality of crops. However, unfortunately, in practice what often happens is that if one beneficial trait is gained (e.g. stress resilience), it can be at the expense of another trait (e.g. crop yield or quality).

A number of approaches and developments are highlighted below.

Pesticides (e.g. insecticides, fungicides and bactericides) are commonly used agents to protect seeds or plants from pests and/or diseases. They typically act through toxicity to the pest or disease, and in theory are not intended to harm the host seed or plant. Yet there are clear problems with pesticides including toxicity to non-target insects, fungi or bacteria. Therefore, their use can damage the overall ecosystem, much of which is symbiotically beneficial for general plant life. Effectiveness of pesticides can also diminish over time due to a build up of resistance from the pest/disease. Additionally, consumers are becoming less tolerant with the use of pesticides because of potential harmful effects to people.

Genetic modification has also been employed to improve genotype and resulting phenotypic traits of plants, particularly through transgenic insertion of a pest resistance-associated gene(s) into a plant genome. Whilst some studies and commercial products have shown promise, there are still many unknowns and there is an overwhelming distrust from the public. Selective breeding is a form of genetic modification, and this has been used for centuries to identify and select for beneficial plant traits for subsequent breeding purposes. Whilst this has generally worked well, and the public, generally speaking, considers this to be an acceptable form of manipulation, it also can have its downfalls, including duration of time required to see beneficial results, loss of other phenotypic traits, and so forth.

With a greater understanding of plant biochemistry and genetics in the past few decades, researchers have turned to boosting the plant's own defence mechanisms, primarily through triggering or providing the plant with signalling molecules. By inducing or providing the signalling molecule, this can then result in triggering a natural cascade reaction in a plant, leading to a desirable trait. A good example of this is jasmonic acid, which has been used as an external foliar spray or root drench to induce pest resistance in crops. Yet, due to the high cost of the compound it is not commercially viable.

More-so, adding chemical agents can sometimes be deleterious on another biochemical pathway or cause a negative phenotype, much the same way as a therapeutic drug given a human almost will always has a negative side effect. To use the same example of jasmonic acid, it was found to damage the crop. A further disadvantage is that some signalling molecules can be genus- or species-specific, so although a trait can sometimes be improved in a certain plant, it may not be applicable to other plants. Furthermore, there still can be a negative public perception of chemical agents added to seeds or plants.

Other studies have focused on physical treatments on seeds or plants to improve plant performance and subsequent yield/quality of crops. The aim here has been to move away from chemical agents or pesticides for many of the reasons outlined above.

As outlined in U.S. Pat. No. 8,001,722, physical treatments of seeds have included application of hot water, hot air, UV-C, X-rays, gamma rays, and electron beam irradiation. Yet, these have been primarily used simply to disinfect seeds from plant pathogens and insects, not to improve a seed or plant's systemic stress resilience and overall plant performance over time.

To elaborate on UV-C irradiation (the focus of U.S. Pat. No. 8,001,722) the patent discusses that, conventionally, UV-C irradiation has been shown to elicit resistance of various fruits and vegetables to post-harvest decay, delay of ripening, and enhance plant pest resistance through the Systemically Acquired Resistance (SAR) pathway in the plant. Yet, although pest resistance can be improved to some degree, it was found in other reported studies that UV-C results in a decrease in plant performance (fewer shoots and ears, and lower seed production).

The discussion in U.S. Pat. No. 8,001,722 then shifts to the apparent invention as was claimed, which was the ability for UV-C treatment of the seed for sowing to be used to increase yield of harvested seed when the UV-C treatment is combined with chemical pesticides (Maxim XL, Apron XL and Trilex). However, this does not overcome a primary issue of using pesticides. Furthermore, in assessing the results of this patent, it is clear from Example 3 that UV-C irradiation alone has substantially no beneficial effect on plant yield. In fact, in two of the three varieties tested, there was an overall negative effect on yield due to the administration of UV-C to the seeds. This is in agreement with conventional wisdom that UV-C treatment can be damaging and is viewed consistently as a typical germicidal, DNA damaging stimuli, and does not lead to improved yield and/or quality.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Further aspects and advantages of the present invention will become apparent from the ensuing description which is given by way of example only.

SUMMARY

According to one aspect of the present invention there is provided a method of treating a seed for sowing to improve subsequent plant performance
characterised by the step of:
a) treating the seed for sowing with UV-B irradiation.

According to another aspect of the present invention there is provided a method of treating a seed for sowing to improve plant performance
characterised by the step of:
a) treating the seed such that the seed, a resulting plant and/or a resulting harvestable crop material has increased levels of flavonoids compared to an untreated seed; or
b) treating the seed such that the seed, a resulting plant and/or a resulting harvestable crop material has increased gene transcription level or protein expression level resulting in increased flavonoid concentration therein.

According to another aspect of the present invention there is provided a method of improving plant performance
characterised by the step of, in a seed for sowing, a resulting plant or a harvestable crop material:
a) selecting for increased levels of flavonoids;
b) selecting for increased gene transcription level or protein expression level associated with increased flavonoid concentration therein.

According to a further aspect of the present invention there is provided a seed for sowing
a) characterised in that the seed for sowing has been treated with UV-B irradiation.

According to a further aspect of the present invention there is provided a plant or harvestable crop material derived from at least one seed for sowing
characterised in that the at least one seed for sowing has been treated with UV-B irradiation.

According to a further aspect of the present invention there is provided a seed for sowing
characterised in that the seed for sowing has one or more of the following:
a) an increased level of flavonoids compared to normal or a non-induced state;
b) an increased level of UV-B mediated gene(s) and/or protein product(s) compared to normal or a non-induced state; and/or
c) an increased gene transcription level or protein expression level associated with increased flavonoid concentration therein compared to normal or a non-induced state.

According to a further aspect of the present invention there is provided a plant or harvested crop material
characterised in that the plant or harvested crop material has one or more of the following:
a) an increased level of flavonoids compared to normal or a non-induced state;
b) an increased level of UV-B mediated gene(s) and/or protein product(s) compared to normal or a non-induced state; and/or
c) an increased gene transcription level or protein expression level associated with increased flavonoid concentration therein.

As will be elaborated on further below, the Applicant has identified that, compared to untreated samples, seeds treated with UV-B irradiation provide substantially improved biological outcomes linked with plant performance (namely increased flavonoid concentration as discussed below), and in preliminary trials also showed improved yield of harvestable crop material after 30 days.

For reasons outlined below, it is expected that these results may be seen over a wide number of seed types and plants after treatment with UV-B irradiation according to the present invention.

The present invention avoids the need for pesticides and chemical additives to improve plant resistance and performance. It also may help to overcome a significant hurdle as illustrated with regards to UV-C treatment of seeds, which is shown to actually decrease crop yield (literature and the Applicant's own trials (not shown) both show UV-C treatment causes irreversible damage to plants) despite possibly increasing pest resistance to some extent (Vallad and Goodman 2004, Crop Sci; Heil et al., 2001, Journal of Ecology).

DEFINITIONS AND PREFERRED EMBODIMENTS

Throughout this specification the term seed for sowing should be taken as meaning any embryonic plant prior to, and/or intended to be used for, planting to grow any form of plant life or crop for subsequent use (typically, but not solely, for human and animal consumption).

Substantially any type of seed may be used according to the present invention, of which there are currently about 35,000 types currently known worldwide, as noted in U.S. Pat. No. 8,001,722. Based on further discussion and reference to supportive scientific literature, it is fair to assume that the preliminary results seen thus far strongly support that UV-B treatment of seeds may be used to improve plant performance across substantially any plant species.

Preferably, the seed for sowing is selected from the group consisting of lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat and combinations thereof.

Throughout this specification, the term plant performance should be taken as meaning improving:
a) stress resilience to one or more environmental stresses to the seed and/or resulting plant and/or resulting crop before or after harvesting, and/or
b) improving yield of harvestable crop material; and/or
c) improving quality of harvestable crop material.

Preferably, improved stress resilience is selected from the group consisting of improved drought resistance, salinity stress, transplantation shock, long-term hardiness, high visible light stress, insect pest stress, fungal or bacterial stress, and/or other disease-related stress. The term long-term hardiness should be taken as meaning the ability of a plant to withstand one or more stresses during crop production and to allow desirable yield and/or quality of the plant at harvesting. Methods of improving long-term hardiness were the subject of a previously filed New Zealand Patent Application (NZ 622482) filed on 14 Mar. 2014, the contents of which are hereby incorporated into the present application by reference.

For example, improved yield may be measured by weight of harvestable crop material, such as lettuce leaves, soybeans, tomato fruit, in comparison to harvestable crop material where the seeds for sowing were not treated with UV-B. Alternatively, an improved yield may be measured by fresh shoot weight or whole plant dry weight.

In a further embodiment, improved yield may be an improved germination of seeds resulting from the treatment method. In yet a further embodiment, an improved yield may be an improved water use efficiency of the resulting plant.

For example, improved quality may be assessed as a quantitative or qualitative assessment on any one or combination of a lack of blemishes on the crop (either internal or on the surface, typically from insects), improved shelf life, improved resistance to bruising or other post-harvest handling, lack of deformities or irregular shapes/sizes, improved taste, size, shape, colour, texture, and so forth.

An advantage of the present invention is that, in preliminary trials, both stress resilience and plant yield were observed (often these traits can work in an inverse relationship, where resilience is achieved at the cost of yield—as seen with UV-C treatment).

Throughout this specification the term ultraviolet (UV) irradiation should be taken as meaning electromagnetic radiation with a wavelength shorter than visible light, but longer than X-rays, and is in between the range of 10 nm to 400 nm (corresponding to 3 eV to 124 eV). The UV radiation spectrum is considered to be invisible to humans, and therefore differentiated from visible light in the spectrum of about 400 nm to 700 nm.

Throughout this specification, the term UV-B radiation should be taken as meaning radiation specifically within the waveband of 320 nm to 280 nm (herein described as the UV-B range). This is distinguishable from the UV-C waveband (280 to 100 nm) and UV-A waveband (400-320 nm). It should also be distinguishable from natural sunlight which although provides UV-B radiation, also includes other UV radiation.

Preferably, the UV-B radiation is administered via LED lights.

Preferably, the UV-B radiation is administered in the UV-B waveband of between 320 to 280 nm.

The trials conducted by the Applicant have shown different treatments peaking at wavelengths in this UV-B waveband provide beneficial plant performance results.

More preferably, the UV-B radiation is administered in the UV-B waveband at approximately 286 nm (±5 nm).

The trials conducted by the Applicant showed that the UV-B radiation administered at approximately 286 nm showed a number of beneficial plant performance results.

Alternatively, positive results were still observed when treated the seeds for sowing at approximately 317 nm, as exemplified in Example 15.

LED lights are configured to administer a peak irradiance wavelength of light, for instance at 286 nm. It should be appreciated that use of a device to perform the present invention may be carried out according to the previously filed New Zealand patent application number 621039 filed on 10 Feb. 2014 by the same application, the entire contents of which are hereby incorporated into the present application by reference.

In preliminary trials, the UV-B irradiation was administered for about 40 minutes.

Whilst this was shown to produce good results, the Applicant envisages that the length of time of UV-B irradiation may be modified (reduced/increased) depending on the application, and in particular with different seed hydration protocols.

The treatment may either be a single or multitude time point treatment. For instance, the Applicant has tested dosing the seeds with UV-B irradiation at about 24 hr following initial water hydration, which was shown to work well. However, it should be appreciated that the particular time point of administration should not be a limitation of the invention.

Preferably, the UV-B irradiation is administered following and/or during a seed priming process.

For example, the seed priming process may include treatment with an osmoticum such as PEG8000 which helps to manage the seed hydration process.

Preferably, the UV-B irradiation is administered following an initial water hydration process. Different levels of hydration may be fine-tuned during treatment regimes.

Both preferred treatment regimes (seed priming with an osmoticum, and/or water hydration) were shown to work well in the preliminary trials. However, it should be appreciated that the regime may vary substantially without departing from the scope of the invention.

Also, it should be appreciated that the UV-B treatment may be initiated at different time-points or durations. For instance, UV-B treatment may be applied prior to seed hydration, germination, and/or during initial germination (e.g. following moisture application for seed germination), and/or during a coating/seed priming treatment.

Preferably, the UV-B treatment method for seed for sowing includes a dosage in the range of 0.01 to 368 kJ m$^2$, utilizing an irradiance range of $3.19 \times 10^{-5}$ W cm$^{-2}$ s$^{-2}$ to $1.42 \times 10^{-4}$ W cm$^{-2}$ s$^{-2}$. It should be noted that due to the very strong biological effectiveness of UV-C wavelengths in generating DNA damage and physiological damage, a much larger UV-B dosage may be applied by comparison. Dosage may change in relation to treatment protocols such as hydration protocols.

Preferably, the UV-B treatment method for seed for sowing includes a dosage in the range of 0.1 to 12 kJ m$^2$.

In an alternative embodiment, the UV-B treatment is applied to a plant prior to seed harvest from the plant to be subsequently used for sowing. It should be appreciated that the effective dosage for a growing plant may differ to that of a harvested seed due to differences in physiology.

Preferably, the method includes co-administration of UV-B irradiation with either visible light.

More preferably, the visible light is blue and/or red light.

In particular, the Applicant considers that visible light (e.g. blue and or red light) may improve one or more aspect of plant performance, such as crop yield. Preliminary results show slight increases in yield due to visible light treatment of seeds, and therefore it may be assumed that when combining this with the UV-B treatment (where significant results were seen), an additive or potentially a synergistic effect might be observed.

In another embodiment, the method includes co-administration of UV-B irradiation with UV-A treatment of a seed for sowing.

Although by no means essential, this co-treatment with UV-A may be useful in improving quality of the harvestable crop material (e.g. pigment production).

In a further alternative embodiment, the UV-B treatment is applied to a plant prior to seed harvest from the plant for subsequent plant breeding applications as opposed to plant/crop performance.

These two embodiments illustrate that the UV-B treatment effectively is still being applied to seeds, but whilst still connected to the plant. Such embodiments, and others, should be considered to still fall within the scope of the invention.

Throughout this specification the term harvestable crop material should be taken as meaning any material from the plant which may be harvested to be used for subsequent purposes or human or animal consumption. The crop material may be harvested seeds, which may be consumed as food or alternatively used for subsequent plantation or breeding purposes. The harvested material may be a fruit, a vegetable, a tree, a shrub, a grass, a herb, and so forth. It may also be an extract or component of any one of the above crop materials. It should also be appreciated the present invention need not be limited to material that is actually harvested, and may alternatively be used to simply build plant performance without any harvesting. A good example of this could be forest regeneration, never intended to be farmed.

Preferably, the harvestable crop material is selected from the group consisting of lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat and combinations thereof.

The Applicant considers that these crop materials (as of course the seeds) are probably the most commercially important crops for which the present invention may be applied.

Additionally, as noted elsewhere in the specification, the systems regulating UV-B specific gene signalling are known to be closely conserved across these plants (and others), so there is good support that UV-B radiation treatment of seeds may produce the same beneficial effects on these different commercially important crop materials.

Secondary Metabolites and Genetics

First, it should be appreciated that there is no current knowledge of UV-B photomorphogenic responses in seeds. Seeds are an entirely different developmental entity to a growing plant. More-so, there is no knowledge if a UV-B photoreceptor is even functioning in a seed in response to UV-B, nor whether there is a response in a seedling being induced by any UV related seed treatment.

Throughout the specification, the term flavonoid should be taken as a class of plant secondary metabolites which have the general structure of a 15-carbon skeleton, consisting of two phenyl rings and heterocyclic ring (C6-C3-C6).

Preferably, the UV-B treatment according to the present invention causes an increased concentration of a least one flavonoid in the seed for sowing, plant or harvestable crop material.

Flavonoids are widely found in plants and have diverse functions, including pigmentation. Additionally, they also act as chemical messengers, physiological regulators, and cell cycle inhibitors. There is significant research on the complex nature of flavonoids and their involvement in biochemical pathways in plants.

Different stimuli can regulate a wide variety of secondary metabolites including a wide variety of different flavonoids. In plants, there is evidence that UV-B light (and particular wavelengths therein), produce distinct responses in terms of certain types of flavonoids, related secondary metabolites and positive performance (Wargent et al., 2014. Plant Cell and Environment). Based on the new data provided in this patent application, the Applicant hypothesizes that it may also be some or all of the same heightened flavonoids measured in the seeds and plant material that are at least partly responsible for the increased plant performance observed.

Preferably, the flavonoids which are increased in concentration are selected from the group consisting of quercetins, cyanidins, kaempferols and combinations thereof.

These flavonoid types are known to be up-regulated in plants following UV-B stimulus. Again, it is emphasized that no literature has made any link that UV-B treatment of seeds may similarly cause up-regulation of these or similar flavonoids in the seeds, or resulting seedlings, plants or harvestable crop material.

Without wishing to be bound by theory, the Applicant envisages the UV-B radiation treatment in seeds may actually be resulting in a positive feedback loop at some level in the resulting seed, seedling and/or plant, such plant performance is synergistically improved long-term from the initial seed treatment.

As noted above, flavonoids are an indicator or marker for heightened plant resilience to various abiotic and biotic stresses in a wide variety of plants (e.g. drought stress, high visible light stress, insect pest damage and fungal infection), improved plant performance, and increased crop yield and quality. The preferred flavonoids listed herein are those which have been seen in response to UV-B treatment in plants (not seeds).

Without wishing to be bound by theory, the Applicant considers it possible that some or all of these certain types of flavonoids are directly leading to the increased plant performance being observed following UV-B seed treatment.

Furthermore, the Applicant considers that an increase in flavonoids may provide protection to a plant in a wide variety of ways as it undergoes onward growth and development (Rozema et al., 1997. Trends in Ecology & Evolution).

Preferably, the UV-B treatment according to the present invention causes an increase in levels of at least gene transcription and/or protein expression related to flavonoid production.

Preferably, the UV-B treatment leads to:
a) an increased activity of UV RESISTANCE LOCUS 8 (UVR8), e.g. UVR8 protein monomerisation,
b) an increased gene expression of chalcone synthase (chs),
c) an increased gene expression of constitutively photomorphogenic 1 (cop1), and/or
d) an increased gene expression of elongated hypocotyl 5 (hy5).

These preferences are based on literature available for plant genetics (not seeds) which was generally understood by the Applicant before arriving at the present invention. Yet, it should be appreciated that whilst there is a large amount of data available on plants, no one in the industry has suggested or hypothesized that the same or similar cascade might be occurring in seeds as a result of targeted UV-B treatment, nor that such a system could be beneficially manipulated to achieve not only improved stress resilience, but also improved crop yield and or quality.

It is known that uv resistance locus 8 (uvr8) is a key gene in UV-B light signalling in plants, responsible for the UV-B mediated expression of numerous genes involved in plant form and function (Favory et al., 2009. Embo Journal). Therefore, UVR8 activity may be considered key to the beneficial response.

In plants, studies show the initial signalling cascade triggered by UVR8 involves monomerisation of the UVR8 protein [from a homodimer ground state], and subsequent heterodimerisation with the E3 ubiquitin ligase constitutively photomorphogenic 1 (cop1) protein [COP1], and then interaction with the bZIP transcription factor elongated hypocotyl 5 (hy5) (Rizzini et al., 2011. Science). This signalling complex is seen as at least one marker of the activation of UV-B photomorphogenesis in plants. Therefore, based on the results seen (namely raised concentration of flavonoids and subsequent plant performance in UV-B treated seeds (but not UV-A, and/or red/blue treated seeds), the Applicant now suggests that the same signalling cascade may be responsible in either the seeds and/or resulting plant/harvestable crop material. As far as the Applicant is aware, there is no prior art which reports UVR8 playing an active role in a seed response in some manner.

Furthermore, in plants (again, not seeds), studies show that at least one gene which is regulated by UV-B light in leaves is chalcone synthase (chs). chs codes for a key committed step in the biosynthesis pathway of a large group of plant secondary metabolites, including the flavonoids (Jenkins, 2009. Annual Review of Plant Biology).

It is known that those systems regulating UV-B specific signalling is widely found across plant taxa. Conservation of the uvr8 locus is observed in angiosperms, mosses and green algae (Rizzini et al., 2011. Science; Wu et al., 2011. Journal of Chemical Information and Modeling). It is therefore expected that manipulation of UV-B photomorphogenesis as described here may be achieved in all crop plant species.

Therefore, without wishing to be bound by theory, the Applicant foresees that following seed treatment with UV-B, there may be a distinct signalling pathway initiated by at least uvr8 (or a related pathway) which subsequently leads to expression of certain flavonoids and other secondary metabolites, which may be linked to the improved plant performance being observed from the present invention.

Some preliminary trials have been performed by the Applicant to assess which gene(s) and/or which flavonoids may be being up-regulated as a result of the UV-B treatment, and which might be primarily responsible for the improved plant performance. Trials performed by the Applicant (see Example 13) has shown that the uvr8 locus and increased activity of UVR8 is contributing to the improved plant performance as a result of the UV-B treatment.

In summary, it should be appreciated that the Applicant has identified a way to improve plant performance through UV-B treatment of seed for sowing (including harvestable seeds for sowing). Now, with the subsequent understanding that the UV-B treatment of seeds leads to improved plant performance most likely through a gene signalling pathway and increased flavonoid concentration (and the downstream effects of such), it suggests to the Applicant the same result may potentially be achieved (or selected for) by non UV-B treatment (for instance through genetic breeding or genetic modification to up-regulate a specific gene or combination of genes), which similarly triggers the same signalling pathways in seeds and/or plants associated with these flavonoid markers and/or gene expression profiles.

SUMMARY OF ONE OR MORE ADVANTAGES OF THE PRESENT INVENTION MAY INCLUDE

The invention increases plant performance, both in relation to stress resilience and plant yield (often these traits can work in an inverse relationship, where resilience is achieved at the cost of yield—as seen with UV-C treatment).

Results show an increased expression level of flavonoids both in seeds and in resulting plant material tested following treatment (associated with various stress resilience pathways conserved across wide plant taxa), therefore meaning the method is expected to work for all crop plant species through an apparent common mode of action.

Results show a significant increase in plant productivity following seed treatment.

The flavonoid (and/or other secondary metabolite) markers thought to be attributed to the UV-B specific effects are closely linked to certain genes which are known to be responsible for UV-B mediated expression, opening up further opportunities for alternative seed treatment methods, selective breeding and/or genetic manipulation.

The invention (and results seen) does not rely on any additional pesticide or chemical treatment.

The invention (and results seen) does not rely on use of UV-C radiation, which is known to cause irreversible damage to plants.

UV-B radiation is naturally provided in sunlight, and therefore the seed treatment should have a wide consumer acceptance level.

The specific dosages and time of treatment may be adaptable to suit particular seed types or objectives of the grower.

A seed treatment may be particularly beneficial in providing a more exact treatment, reducing the likelihood of mis-dosage which could happen with a plant seedling treatment.

Treating seeds allows for a broad range of crops to be treated, such as row crops, for which there is no current technical approach to treat such outdoor crops with a UV treatment.

As of yet, no substantial side effects have been observed.

UV-B treatment is relatively cost effective, and can be achieved using standard LED lights.

BRIEF DESCRIPTION OF THE DRAWINGS

Further aspects of the present invention will become apparent from the following description which is given by way of example only and with reference to the accompanying drawings in which.

DETAILED DESCRIPTION

Example 1

Analysis of Flavonoid Levels in Seeds Following UV-B Treatment

In this example, seeds were exposed to a UV-B treatment, and were then frozen for analysis of UV-B absorbing secondary metabolites in the seed themselves.

Seeds of the variety Legacy (Egmont Seeds, New Zealand) were spread on water soaked filter paper. Seed were then exposed to a narrow-band UV-B dosage peaking at 286 nm using an LED (Light Emitting Diode) array for 40 min. As a control, seeds were exposed to a visible light dosage only, composed of blue and red light LEDs for 40 min. Seed were exposed to light dosages at different time-points following initial water imbibing of seed (0 h, 24 h). The seeds were kept at 16° C. between treatments, and until the end of the trial at 48 h, when seed were frozen in liquid nitrogen for UV-B absorbing compound analysis. Analysis of UV-B absorbing compounds (presumptive flavonoids) was carried out by homogenization of seed in acidifed methanol, centrifugation, and measurement of supernatant absorbance by spectrophotometer at 300 nm.

Figure 1:
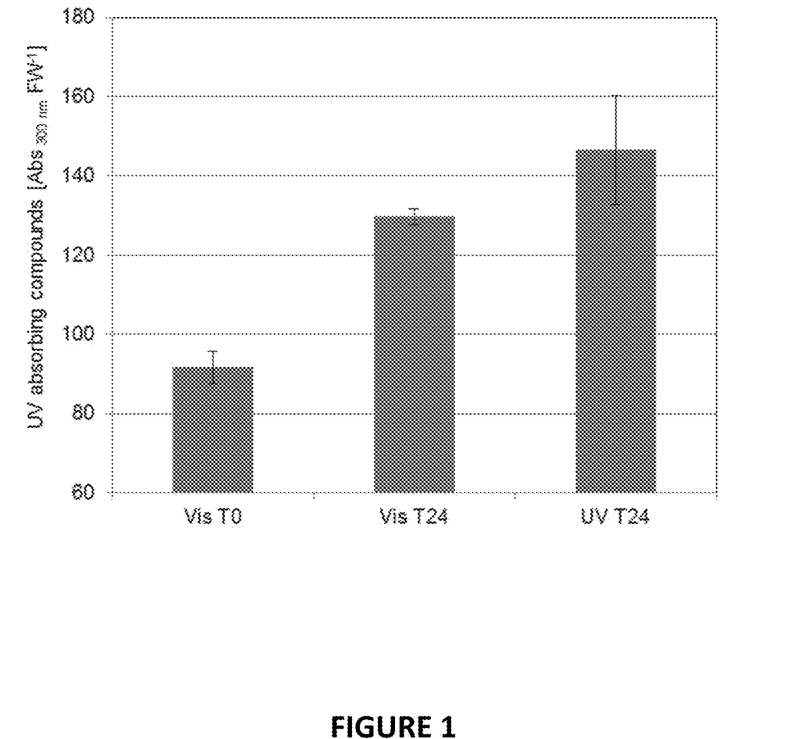
FIG. 1 Analysis of Flavonoid levels in seeds following UV-B treatment.

The results are shown in FIG. 1, depicting seed levels of UV-B absorbing compounds [at 300 nm; presumptive flavonoids] of Legacy lettuce immediately after UV-B treatment. Seeds were maintained under visible light only conditions ('Vis') or a UV-B treatment at 286 nm ('UV'). Treatments were applied at the times indicated after seed were imbibed with water (T0=at time of imbibing; T24=24 h after imbibing). Flavonoids are 18% higher in UV T24 seed compared to Vis T24 seed, and flavonoids are 60% higher in UV T24 seed compared to VIS T0 seed. Values presented are means of three replicate lots per treatment, with each lot consisting of 80 individual seed; 1 S.E. It can be seen that an increase in presumptive flavonoids (detected at 300 nm) are seen after 24 hours after treatment in both samples (UV-B and visible light). However, the level of flavonoids are substantially increased in the UV-B treated sample compared to the visible light treated sample at the same 24 hr time point. This increase is thought to be due to UV-B specific flavonoid production as discussed previously. Further tests hope to confirm this.

Example 2

Analysis of Flavonoid Levels in Ezmina Lettuce Plant Leafs 20 Days after UV-B Seed Treatment In this example, seeds were exposed to a UV-B treatment, and were then germinated, transplanted onto soil, and grown to a certain age, prior to assessments of leaf polyphenols being made.

Lettuce seeds of the variety Ezmina (Enza Zaden, Netherlands) were spread on water soaked filter paper. Plants were then exposed to a narrow-band UV-B dosage peaking at 286 nm using an LED (Light Emitting Diode) array for 40 min. As one control, seeds were exposed to a visible light dosage only, composed of blue and red light LEDs for 40 min. Seed were exposed to light dosages at different time-points following initial water imbibing of seed (0 h, 24 h). A second form of control consisted of seeds being wrapped in aluminium foil and not exposed to any light.

Germinating seeds were then transferred onto soil, and following seedling propagation, plants were maintained in outside ambient conditions for 10 days. Following this time period, non-invasive measurements of leaf flavonoid levels were made with a Dualex Scientific polyphenol meter (Force-A, Paris).

Figure 2:
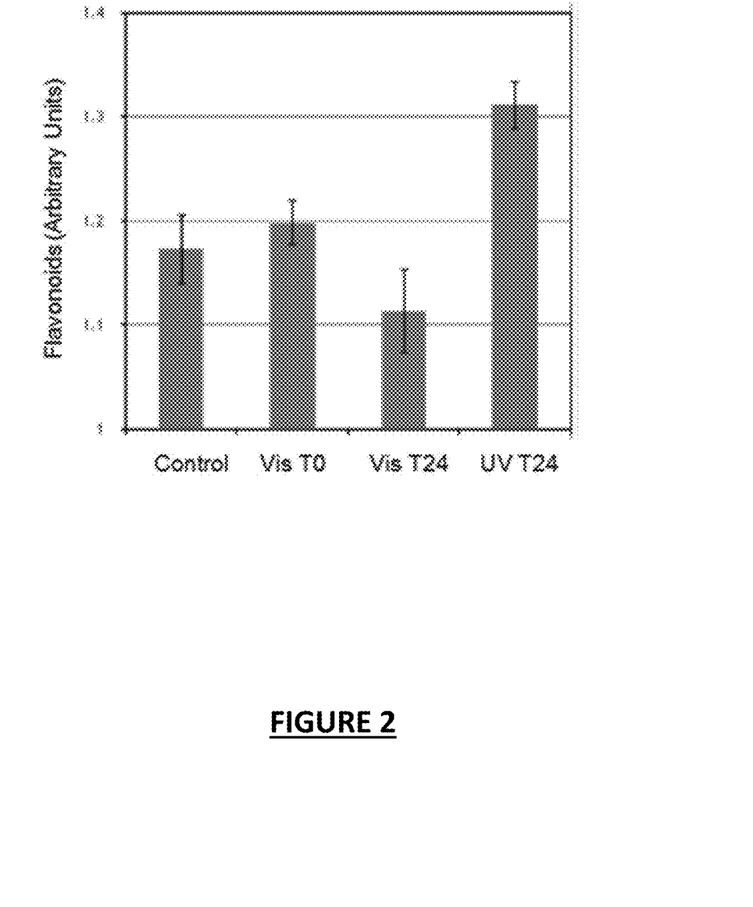
FIG. 2 Analysis of Flavonoid levels in Ezmina lettuce plant leaves 20 days after UV-B seed treatment, and FIG. 3 Analysis in plant productivity (measured by fresh shoot fresh weight) following UV-B treatment.

The results are shown in FIG. 2, which measure flavonoid levels 20 days after seed treatments. This FIG. depicts leaf flavonoid levels of Ezmina lettuce plants 20 days after seed treatment. Seeds were maintained under dark foil wrapped conditions ('Control'), visible light only ('Vis'), or a UV-B treatment at 286 nm ('UV'). Treatments were applied at the times indicated after seed were imbibed with water (T0=at time of imbibing; T24=24 h after imbibing). Flavonoids are significantly higher in UV T24 plants according to Analysis of Variance (P<0.05). Values presented are means of 11-24 plants according to individual treatments, ±1 S.E. The UV-B treated sample showed significantly higher flavonoid levels at 20 days compared to the visible light sample at 20 days, either if treated at 24 hours and 0 hours. Interestingly, the flavonoid level at 20 days in the sample treated with visible light at 24 hours actually was lower compared to the levels when treated at the zero time point. This study illustrates a relationship between the UV-B induced flavonoid concentration seen in seeds and the resulting plant material.

Example 3

Analysis in Plant Productivity (Measured by Fresh Shoot Fresh Weight) Following UV-B Treatment In this example, seeds were exposed to a UV-B treatment, and were then germinated, transplanted onto soil, and grown to a certain age, prior to assessments of plant shoot fresh weight being made, as an indication of plant yield following seed treatment.

Seeds of the variety Legacy (Egmont Seeds, New Zealand) were spread on water soaked filter paper. Seed were then exposed to a narrow-band UV-B dosage peaking at 286 nm using an LED (Light Emitting Diode) array for 40 min. As a control, seeds were exposed to a visible light dosage only, composed of blue and red light LEDs for 40 min. Seed were exposed to light dosages at different time-points following initial water imbibing of seed (0 h, 24 h). Following treatment, seed were transferred onto soil, and grown for 30 days. Shoot fresh weight of plants (i.e. above ground biomass) was then assessed as an indication of plant yield.

Figure 3:
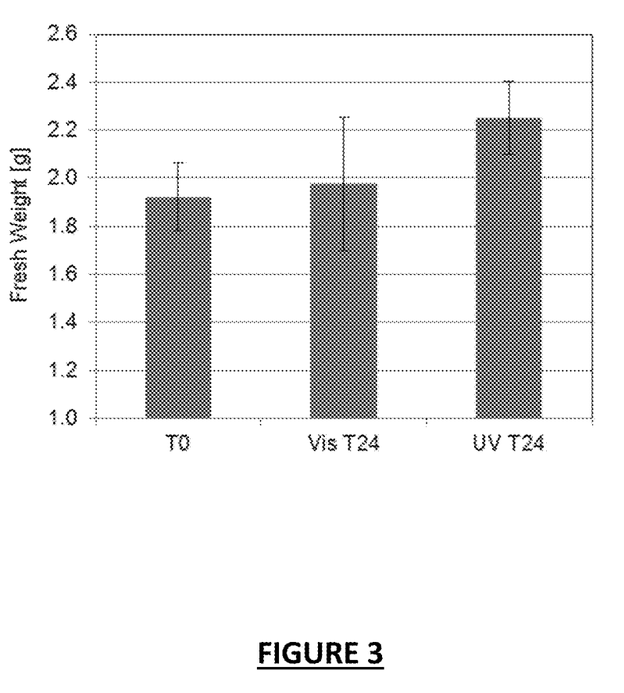

The results are shown in FIG. 3. This FIG. shows shoot fresh weight of Legacy lettuce plants 30 days after seed treatment. Seeds were maintained under visible light only conditions ('Vis'), or a UV-B treatment at 286 nm ('UV'). Treatments were applied at the times indicated after seed were imbibed with water (T0=at time of imbibing; T24=24 h after imbibing). Bar displayed for 'T0' treatment is based on both visible light and UV treatments values. Average fresh weight in 'UV T24' plants is increased by 17% compared to 'T0' control plants. Values presented are means of six replicated plants per treatment, ±1 S.E. As observed that in the UV-B treated samples, average fresh weight in plants is increased by 17% compared to control plants. A very marginal increase can be observed in plants treated with visible light compared to control plants. This result illustrates the advantage of increased plant performance and in particular crop yield. It bridged a potential connection with the increased concentration flavonoids seen in both the seeds and resulting plant, and it is expected that certain types of flavonoids may be responsible for this effect, as discussed previously. Further trials are being performed to confirm this.

Example 4

Analysis of Leaf Flavonoids in Kale (*Brassica* Forage Crop)

In this example, kale seedlings were treated with UV-B prior to sowing, and another set of seedlings grown from seed were not treated with UV-B.

Kale (*Brassica oleracea* var. Regal) seeds were first primed by being immersed in a PEG8000 solution (−1.25 mPA) and kept in the dark at 16° C. After 20 h, seeds were irradiated with 500 µmol m$^{-2}$ s$^{-1}$ of continuous red/blue light. 50% of these seeds were additionally treated with 3.19×10$^{-5}$ W cm$^{-2}$ s$^{-1}$ UV-B light supplied by a UV-LED source, the transmittance of which peaked at 286 nm. After 28 h of continued treatment (total priming duration 48 h), seeds were removed and air-dried for 72 h at 16° C. Seeds were then sown and grown in PEG8000 (−1.25 mPA, 400 ml) to induce drought stress. After 3 weeks of continued drought stress, leaf flavonoid concentrations were determined using a Dualex Scientific+ chlorophyll and polyphenol meter (Force-A, Orsay, France).

The results are shown in Table 1 below. There was a 12% increase in leaf flavonoids in kale seedlings where seeds were treated with UV prior to sowing, compared to seedlings grown from seed which were not treated with UV prior to sowing.

TABLE 1

|  | Control | S.E. | UV-treated | S.E. | Increase in UV-treated compared to control (%) |
|---|---|---|---|---|---|
| Flavonoid Index | 0.61 | 0.03 | 0.7 | 0.02 | 12* |

*statistically significant increase at P < 0.05

This supports that the resultant plant following UV-B seed treatment has increased levels of flavonoids compared to an untreated seed.

Example 5

Analysis of Drought Stress

In this example, a drought stress was applied to kale plants from the point of seed germination. One group of seeds were UV-B treated, and another group was not treated with UV-B.

Kale (*Brassica oleracea* var. Regal) seeds were immersed in water and kept in the dark at 16° C. After 4 h, seeds were irradiated with 500 µmol m$^{-2}$ s$^{-1}$ of continuous red/blue light. 50% of these seeds were additionally treated with 1.42×10$^{-4}$ W cm$^{-2}$ UV-B light supplied by a UV-LED source, the transmittance of which peaked at 286 nm. After 30 h of treatment, seeds were air-dried for 72 h at 16° C.

Seeds were then subjected to a drought stress during germination. UV-primed and control seeds were germinated in either water or one of 2 concentrations of PEG8000 (−1 mPA 'Drought', −1.5 mPA 'Severe drought'). After 72 h, seedling weight and radicle length were quantified.

The results are shown in Table 2 below. After drought stress, emerging kale seedlings from seeds that had been UV-B treated, accumulated more biomass and displayed longer radicle lengths 72 hr after sowing, compared to seedlings sown from seed that were not treated with UV prior to sowing.

TABLE 2

|  | Medium | UV-treated | S.E. | Control | S.E. | Increase in UV-treated compared to control (%) |
|---|---|---|---|---|---|---|
| Radicle length (mm) | Well-watered | 9.1 | 0.6 | 7.4 | 0.9 | 24 |
|  | Drought | 8.3 | 0.6 | 6.9 | 0.7 | 20 |
|  | Severe drought | 6.8 | 0.8 | 5.7 | 0.6 | 20 |
| Biomass (mg) | Well-watered | 18.3 | 0.8 | 14.1 | 0.7 | 30** |
|  | Drought | 14.8 | 0.6 | 12.9 | 1.0 | 15 |
|  | Severe drought | 13.1 | 0.5 | 11.7 | 0.7 | 13 |

**statistically significant increase at P < 0.001

This trial supports that UV-B seed treatment provides protection against yield-limiting stresses encountered in the growing environment, such as drought or salinity stress.

Example 6

Analysis of Seedling Size, Leaf Chlorophyll Level and Nitrogen Index

In this example, kale seed were subject to UV-B treatment and then seedling size, leaf chlorophyll level and relative nitrogen index were all assessed in growing plants, all of which are key indicators of good plant performance.

Kale (*Brassica oleracea* var. Regal) seeds were immersed in water and kept in the dark at 16° C. After 4 h, seeds were irradiated with 500 µmol m$^{-2}$ s$^{-1}$ of continuous red/blue light. 50% of these seeds were additionally treated with 1.01×10$^{-4}$ W cm$^{-2}$ s$^{-2}$ UV-B light supplied by a UV-LED source, the transmittance of which peaked at 286 nm. After 6 h of treatment, seeds were air-dried for 72 h at 16° C. then sown. At 10 days old, plants were assessed for cotyledon leaf size, and at 21 days old, plants were assessed for relative leaf chlorophyll index and nitrogen index, which were determined using a Dualex Scientific+meter (Force-A, Orsay, France).

The results are shown in Table 3 below. There are clear increases in kale seedling growth and plant performance where seeds were treated with UV-B prior to sowing, compared to seedlings grown from seed that were not treated with UV-B prior to sowing.

TABLE 3

|  | Control | S.E. | UV-treated | S.E. | Increase in UV-treated compared to control (%) |
|---|---|---|---|---|---|
| Cotyledon leaf size (mm$^2$) | 113.3 | 5.2 | 120.6 | 5.4 | 6 |
| Chlorophyll index | 18.9 | 0.3 | 19.6 | 0.4 | 4 |
| Nitrogen index | 45.9 | 2.3 | 50.3 | 3.0 | 9 |

Example 7

Analysis of Seedling Weight

Following example 6, the kale seedling weight of seeds treated with UV-B were measured compared to non-treated kale seedlings.

Seed were treated and plants grown exactly as per the methods described for Example 6 above. At 8 weeks old, plants were harvested and leaf area and fresh weights were quantified.

As shown in Table 4, kale plants grown from seeds that were UV-B treated showed a 5% increase in plant weight compared to seedlings grown from non-UV-B treated seeds. Furthermore, the variability of fresh weights within the population was reduced by 36% in UV seed-treated plants, as demonstrated by the reduced standard error (S.E.) values in UV treated resultant plants. This further supports treating a seed for sowing with UV-B radiation improved subsequent plant performance.

TABLE 4

|  | Control | S.E. | UV-treated | S.E. | Increase in UV-treated compared to control (%) |
|---|---|---|---|---|---|
| Shoot fresh weight (g) | 3.75 | 0.14 | 3.94 | 0.09 | 5% |

Example 8

Size Analysis of First Fully Expanded Leaf

In this example, we assessed the 4$^{th}$ fully expanded leaf area in lettuce seedlings in UV-B treated and untreated samples. True leaf growth compaction in young seedlings can be a good indicator of hardiness against future stresses in the growing environment.

Lettuce (*Lactuca sativa* var. Legacy) seeds were immersed in water and kept in the dark at 16° C. After 6 h, seeds were irradiated with 500 µmol m$^{-2}$ s$^{-1}$ of continuous red/blue light. 50% of these seeds were additionally treated with 3.19×10$^{-5}$ W cm$^{-2}$ s$^{-2}$ UV-B light supplied by a UV-LED source, the transmittance of which peaked at 286 nm. After 1 h, 3 h, 6 h of treatment (Seed treatments '1', '2', and '3' respectively; Table 5), seeds were removed and air-dried for 72 h at 16° C. then sown. At 33 days old, the 4$^{th}$ fully expanded leaf area was assessed.

The results are shown in Table 5. We observed a maximum 31% average reduction in size of the 4$^{th}$ fully expanded leaf in lettuce seedlings where seeds were treated with UV prior to sowing, compared to seedlings grown from seed which were not treated with UV prior to sowing.

TABLE 5

| Leaf area (mm$^2$) | Control | S.E. | UV-treated | S.E. | Decrease in UV-treated compared to control (%) |
|---|---|---|---|---|---|
| Seed treatment 1 | 15.6 | 0.9 | 13.8 | 1.0 | 11 |
| Seed treatment 2 | 14.2 | 0.9 | 9.8 | 0.7 | 31** |
| Seed treatment 3 | 16.2 | 1.6 | 15.5 | 1.9 | 4 |

**statistically significant increase at P < 0.001

This initial growth compaction supports the induction of hardiness against future stresses encountered in the growing environment in transplant lettuce seedlings and other crops.

Example 9

Analysis of Dry Weight of Maize Plants

In this example, we treated maize seeds with UV-B radiation, and compared a range of performance parameters of the resulting plants to plants that did not have UV-B treatment of the seeds prior to sowing.

Maize (*Zea mays* var. NZ yellow F1 Hybrid) seeds were immersed in water and kept in the dark at 16° C. After 16 h, seeds were irradiated with 500 µmol m$^{-2}$ s$^{-1}$ of continuous red/blue light. 50% of these seeds were additionally treated with 3.19×10$^{-5}$ W cm$^{-2}$ s$^{-2}$ UV-B light supplied by a UV-LED source, the transmittance of which peaked at 286 nm. After 9 h of treatment, seeds were air-dried for 72 h at 16° C. then sown. Seedlings were harvested at 4 weeks old, and fresh and dry weights of shoots and roots were quantified. Indices for leaf chlorophyll, flavonoid and nitrogen index were assessed using a Dualex Scientific+chlorophyll and polyphenol meter (Force-A, Orsay, France).

The results are shown in Table 6. We saw increases in the whole plant dry weight of maize plants where seeds were treated with UV-B prior to sowing, compared to seedlings grown from seed that were not treated with UV-B prior to sowing. We also observed increases in leaf flavonoid levels, and leaf nitrogen index.

TABLE 6

|  | UV-treated | S.E. | Control | S.E. | Increase in UV-treated compared to control (%) |
|---|---|---|---|---|---|
| Shoot FW (g) | 1.8 | 0.2 | 1.6 | 0.2 | 17% |
| Shoot DW (g) | 0.18 | 0.02 | 0.14 | 0.02 | 26% |
| Root DW (g) | 0.18 | 0.02 | 0.14 | 0.01 | 28% |
| Whole plant DW (g) | 0.36 | 0.04 | 0.28 | 0.03 | 28% |
| Flavonoid index | 0.8 | 0.07 | 0.7 | 0.03 | 4% |
| Leaf nitrogen index | 40 | 7 | 38 | 2 | 6% |

This further supports that treating seeds for sowing with UV-B radiation improves subsequent plant performance.

Example 10

Drought Tolerance and Water Use Efficiency of Lettuce Plants

In a similar study to that seen in Example 5, the authors assessed whether there was an increased physiological tolerance to drought stress imposed on lettuce plants for 11 days following UV-B treatment of the seeds prior to sowing.

Lettuce (*Lactuca sativa* var. Legacy) seeds were immersed in water and kept in the dark at 16° C. After 4 h, seeds were irradiated with 500 µmol m$^{-2}$ s$^{-1}$ of continuous red/blue light. 50% of these seeds were additionally treated with 1.42×10$^{-4}$ W cm$^{-2}$ s$^{-2}$ UV-B light supplied by a UV-LED source, the transmittance of which peaked at 286 nm. After 10 h of treatment, seeds were air-dried for 72 h at 16° C. then sown. After 4 wk, seedlings were transplanted into individual planting cells, each containing 250 ml of potting mix, the maximum water-holding capacity of which was 130 ml. For half of the UV-treated seedlings and half of the control seedlings, the water content of each cell of potting mix was maintained at 130 ml. The remaining plants were subjected to a drought stress, achieved by maintaining the water content of each cell of potting mix at 40 ml. After 11 days of drought stress, stomatal resistance was assessed using a Delta-T porometer (Delta-T Devices, Cambridge, UK), and indices for leaf chlorophyll, flavonoid and nitrogen content were calculated using a Dualex Scientific+ meter (Force-A, Orsay, France).

The results are shown in Table 7. Increased physiological tolerance to drought stress [signified by an increase in stomatal resistance] was indeed observed in the lettuce plants originating from seeds that had been treated with UV-B prior to sowing. An increase in stomatal resistance was also observed in well-watered plants, indicating the potential for plants raised from UV treated seed to exhibit increased Water Use Efficiency (WUE), regardless of the presence of a drought stress.

TABLE 7

| Stomatal resistance (s · cm$^{-1}$) | Control | S.E. | UV-treated | S.E. | Increase in UV-treated compared to control (%) |
|---|---|---|---|---|---|
| Well-watered | 3.0 | 0.4 | 4.2 | 0.4 | 36 |
| Drought stressed | 4.1 | 0.2 | 4.6 | 0.6 | 11 |

This further supports that UV-B seed treatment provides protection against yield-limiting stresses encountered in the growing environment, such as drought or salinity stress. These data also support that UV-B seed treatment may provide increased water use efficiency capability in plants raised from UV treated seed.

Example 11

Salinity Stress on Kale and Lettuce Plants

In another test, kale plants (both from seeds UV-B treated and non-treated seeds) were subjected to salinity stress.

Lettuce (*Lactuca sativa* var. Legacy) and kale (*Brassica oleracea* var. Regal) seeds were immersed in water and kept in the dark at 16° C. After 4 h, seeds were irradiated with 500 µmol m$^{-2}$ s$^{-1}$ of continuous red/blue light. 50% of these seeds were additionally treated with 1.42×10$^{-2}$ W cm$^{-2}$ s$^{-2}$ UV-B light supplied by a UV-LED source, the transmittance of which peaked at 286 nm. After 8 h and 72 h for lettuce and kale respectively, the treatment stopped, seeds were air-dried for 72 h at 16° C., and then sown. After 4 wk, seedlings were transplanted into 250 ml of potting mix, the maximum water holding capacity of which was 130 ml. Half the UV-primed seedlings and half the control seedlings were then subjected to a salt stress (150 mM NaCl; 100 ml administered every 7 days; topped up with water every 3 days) and the remaining seedlings were watered with H$_2$O. After 25 days of salinity stress, plants were harvested and shoot weight was assessed.

The results are shown in Table 8. It can be seen that there is a 13% reduced sensitivity to salinity stress (in terms of salinity-induced reductions in plant fresh weight) in both kale and lettuce plants, where seeds were treated with UV-B prior to sowing, compared to plants grown from seed which were not treated with UV-B prior to sowing.

TABLE 8

| % decrease in growth [in whole shoot fresh weight] under salt stress | Control | UV-treated | Difference between control & UV-treated [%] |
|---|---|---|---|
| Kale | 22 | 9 | 13 |
| Lettuce | 47 | 34 | 13 |

This further shows that UV-B seed treatment provides protection against yield-limiting stresses encountered in the growing environment, such as drought or salinity stress.

Example 12

Analysis of Crop Quality Measured by Leaf Based Pigments of Lettuce

To assess crop quality (e.g. colour, taste, shelf life), leaf-based pigments in a red cultivar of lettuce were assessed following UV-B treatment of seed prior to sowing. Increases in such red pigments as anthocyanins is associated with increased crop quality, taste and shelf-life[1].

[1] Zhang et al. [2013] Anthocyanins Double the Shelf Life of Tomatoes by Delaying Overripening and Reducing Susceptibility to Gray Mold. Current Biology. 23(12): 1094-1100.

Lettuce (*Lactuca sativa* var. Red Oak) seeds were immersed in water and kept in the dark at 16° C. After 3 hr, seed were subjected to 500 µmol m$^{-2}$ s$^{-1}$ of continuous red/blue light with 50% of those seeds additionally receiving 1.42×10$^{-4}$ W cm$^{-2}$ s$^{-1}$ UV-B light, supplied by a UV-LED source, the transmittance of which peaked at 286 nm. 12 h after the initial imbibition process, seeds were removed from water and UV-B treatment. Seeds were air-dried for 72 h at 16° C. then sown. After 35 d, indices for anthocyanins [red leaf pigments] were assessed in seedlings using a Dualex Scientific+ chlorophyll and polyphenol meter (Force-A, Orsay, France). Seedlings were then dried to a constant mass in order to represent anthocyanins per unit (g) plant dry weight.

The results are shown in Table 9 below. Increases in leaf-based pigments in a red cultivar of lettuce were observed from seeds treated with UV-B prior to sowing, compared to plants grown from seed which were not treated with UV prior to sowing.

TABLE 9

| Treatment | Anthocyanin index g DW$^{-1}$ | S.E. | % induction of anthocyanins in plants from UV treated seed compared to control |
|---|---|---|---|
| Control | 0.3196 | 0.01 | — |
| UV-treated | 0.3422 | 0.02 | 7.0 |

These data support that UV seed treatment can increase crop quality characteristics such as colour, taste, shelf-life in plants grown from treated seed.

Example 13

Analysis of Role of UVR8 UV-B Photoreceptor

To assess the underlying genetic response, we studied seedlings raised from a seed genotype lacking functional UVR8 locus [UV-B photoreceptor protein]. Seed of both genotypes were exposed to a UV-B seed treatment and compared with seed that were not treated with UV-B.

*Arabidopsis thaliana* seeds, including the two genotypes 'wild-type' (Landsberg *erecta* or Ler) and the UVR8 null mutant ['uvr8'] were immersed in water and kept in the dark at 16° C. After 12 h, seeds were irradiated with 500 μmol $m^{-2}$ $s^{-1}$ of continuous red/blue light. 50% of these seeds were additionally treated with $6.57 \times 10^{-5}$ W $cm^{-2}$ $s^{-1}$ UV-B light, supplied by a UV-LED source, the transmittance of which peaked at 286 nm. After 4 h of treatment, seeds were air-dried for 72 h at 16° C. then sown. After 32 days of growth, leaf flavonoids were extracted in MeOH:H2O:HCl (70:29:1) and measured by spectrophotometry. Shoots were weighted, ground and clarified by centrifugation and total leaf flavonoids were estimated as Abs300 nm g $FW^{-1}$.

The results are shown in Table 10. It was found that these uvr8 mutant seedlings ['uvr8 KO'] lacked strong induction of leaf flavonoid expression in the growing plant, where the uvr8 seeds were treated with UV-B prior to sowing. Whereas, a marked increase in leaf flavonoid expression [i.e. 29% increase compared to Control] was observed in seedlings following UV-B treatment of seeds with a seed genotype with normal-functioning UVR8 ['WT' or wild-type genotype].

TABLE 10

|  | Control (S.E.) | UV-B treated (S.E.) | % increase from UV treated seed compared to control |
|---|---|---|---|
| Wild-type | 24.48 (2.6) | 31.59 (7.3) | 29 |
| UVR8 | 23.04 (1.8) | 25.51 (4.1) | 11 |

This supports the proposed mode of action for UV-B seed treatment is reliant on the UVR8 locus and UVR8 activity.

Example 14

Increased Seed Germination in Treated Seed

In this example, maize seed were treated with UV-B or not treated with UV-B, with seed germination subsequently assessed.

Maize (*Zea mays* var. NZ yellow F1 Hybrid) seeds were immersed in water and kept in the dark at 16° C. After 20 h, seeds were irradiated with 500 μmol $m^{-2}$ $s^{-1}$ of continuous red/blue light. 50% of these seeds were additionally treated with $3.19 \times 10^{-5}$ W $cm^{-2}$ $s^{-1}$ UV-B light supplied by a UV-LED source, the transmittance of which peaked at 286 nm. After 8 h, 24 h, 32 h of treatment (Seed treatments '1', '2', and '3' respectively; Table 11), seeds were air-dried for 72 h at 16° C. then sown, with germination success subsequently assessed.

The results are in Table 11. It can be seen that germination of seed was improved where seeds were treated with UV-B prior to wetting for germination, compared to seed that were not treated with UV-B prior to sowing.

TABLE 11

| % germination | Control | UV-treated | % improvement in UV-treated seed germination |
|---|---|---|---|
| Seed treatment 1 | 45.45 | 72.73 | 27.28 |
| Seed treatment 2 | 27.27 | 63.64 | 36.37 |
| Seed treatment 3 | 45.45 | 54.55 | 9.1 |
| Average of all treatments | 39.39 | 63.64 | 24.25 |

This supports the use of UV-B treatment of seed to improve germination ability of seed.

Example 15

Use of Another UV-B Peak Wavelength to Improve Seedling Germination Under Drought Stress In a similar study to that seen in Example 5, the authors assessed whether there was an increased physiological tolerance to drought stress imposed during the germination of seed following UV-B treatment of those seed prior to sowing. In this example, a different peak wavelength was used within the UV-B waveband.

Kale (*Brassica oleracea* var. Regal) seeds were immersed in water and kept in the dark at 16° C. After 4 h, seeds were irradiated with 500 μmol $m^{-2}$ $s^{-1}$ of continuous red/blue light. 50% of these seeds were exclusively treated with red/blue light as described before, while the remaining 50% were additionally treated with $1.64 \times 10^{-5}$ W $cm^{-2}$ $s^{-2}$ UV-B light supplied by a UV-LED source, the transmittance of which peaked at 317 nm. After 30 h of treatment, seeds were air-dried for 72 h at 16° C.

Seeds were then subjected to a drought stress during germination. UV-primed and control seeds were germinated in either water or one of two concentrations of PEG8000 (−1, −1.5 mPA). After 72 h, seedling weight and radicle length were quantified.

The results are shown in Table 12 below. After drought stress, emerging kale seedlings from seeds which had been UV-B treated, accumulated more biomass and displayed longer radicle lengths 72 hr after sowing, compared to seedlings sown from seed which were not treated with UV prior to sowing.

|  | Medium | UV-treated | S.E. | Control | S.E. | Increase in UV-treated compared to control (%) |
|---|---|---|---|---|---|---|
| Radicle length (mm) | Well-watered | 6.4 | 0.9 | 7.7 | 0.9 | −17 |
|  | Drought | 11.2 | 1.0 | 5.6 | 0.5 | 99 |
|  | Severe drought | 7.1 | 0.6 | 7.2 | 0.5 | −2 |
| Biomass (mg) | Well-watered | 13.6 | 0.7 | 13.8 | 0.7 | −1 |
|  | Drought | 16.3 | 0.8 | 12.2 | 0.6 | 33 |
|  | Severe drought | 14.9 | 1.0 | 13.5 | 0.9 | 11 |

This example supports that UV seed treatment provides protection against yield-limiting stresses encountered in the growing environment, such as drought or salinity stress, and that the advantages of the invention can be achieved by using a treatment at different wavelengths within the UV-B waveband.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Aspects of the present invention have been described by way of example only and it should be appreciated that modifications and additions may be made thereto without departing from the scope thereof.

What is claimed is:

1. A method of treating a seed for sowing to improve subsequent plant performance comprising a step of treating the seed for sowing using UV-B irradiation, wherein the UV-B irradiation is administered in a UV-B waveband in a range of 291 to 281 nm, wherein a dosage of UV-B is in a range of 0.1 to 386 kJ m$^2$, and wherein a treatment time is 3, 4, 6, 8, 9, 10, 24, 28, 30, 32, or 72 hours.

2. The method as claimed in claim 1, wherein improved plant performance is selected from the group consisting of:
   stress resilience to at least one of environmental stress to at least one of the seed for sowing, resulting plant, and resulting crop before or after harvesting,
   improved yield of harvestable crop material; and
   improved quality of harvestable crop material.

3. The method as claimed in claim 1, wherein the seed for sowing is selected from the group consisting of lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat, and combinations thereof.

4. The method as claimed in claim 1, wherein the UV-B irradiation is administered in a UV-B waveband peaking at 286 nm.

5. The method as claimed in claim 1, wherein the UV-B irradiation is administered following an initial water hydration process.

6. The method as claimed in claim 1, wherein the method comprises co-administration of UV-B irradiation using visible light.

7. The method as claimed in claim 6, wherein the visible light is at least one of red and blue light.

8. The method as claimed in claim 1, wherein the method causes an increased concentration of at least one flavonoid in the seed for sowing, plant, or harvestable crop material.

9. The method as claimed in claim 1, wherein the method causes an increase in levels of at least one of gene transcription, protein expression, and protein activity related to flavonoid production.

10. The method of claim 1, wherein plant performance comprises at least one of an improved resistance to stress caused by weather damage, an improved resistance to stress caused by sun exposure, an improved resistance to stress caused by disease, and an improved resistance to stress caused by insects.

11. The method of claim 1, wherein plant performance comprises at least one of improved taste, size, shape, color, texture, visual appearance, shelf life, and ability to handle post-harvest handling.

12. The method as claimed in claim 4, wherein the UV-B irradiation is administered following an initial water hydration process.

13. The method of claim 1, wherein the seed is from the Asteraceae family.

14. The method of claim 1, wherein the seed is from the Brassicaceae family.

15. The method of claim 1, wherein the seed is from the Poaceae family.

16. The method of claim 1, wherein the seed is lettuce.

17. The method of claim 1, wherein the seed is corn.

18. The method of claim 1, wherein the seed is kale.

19. The method of claim 1, wherein the seed is *Arabidopsis*.

20. The method of claim 1, wherein the seed is selected from the group consisting of lettuce, corn, and kale.

21. The method of claim 1, wherein an irradiance of UV-B is in a range of $3.19 \times 10^{-5}$ to $1.42 \times 10^{-4}$ W cm$^{-2}$s$^{-1}$.

* * * * *